United States Patent [19]

Simioni

[11] Patent Number: 5,668,618
[45] Date of Patent: Sep. 16, 1997

[54] MULTILAYER LENS PARTICULARLY FOR SUNGLASSES

[75] Inventor: Luciano Simioni, Montebelluna, Italy

[73] Assignee: Killer Loop S.p.A., Pederobba, Italy

[21] Appl. No.: 276,141

[22] Filed: Jul. 18, 1994

[30] Foreign Application Priority Data

Jul. 20, 1993 [IT] Italy .................. TV930033 U

[51] Int. Cl.⁶ .................. G02C 7/10; G02C 7/16; A61F 9/02
[52] U.S. Cl. .................. 351/44; 351/45; 2/432; 2/435
[58] Field of Search .................. 351/41, 44, 45, 351/46, 163, 165, 166, 174, 62; 2/435, 13, 12, 431, 432, 433

[56] References Cited

U.S. PATENT DOCUMENTS

| | | | |
|---|---|---|---|
| 1,802,424 | 4/1931 | Hitchiner | 351/165 |
| 1,856,163 | 5/1932 | Jones | 351/163 |
| 3,432,220 | 3/1969 | Schreiner | 351/44 |
| 3,512,880 | 5/1970 | Alexander et al. | 351/45 |
| 3,614,216 | 10/1971 | Rosenthal | 351/44 |
| 3,689,136 | 9/1972 | Atamian | 351/44 |
| 3,700,487 | 10/1972 | Crandon et al. | 117/72 |
| 3,791,722 | 2/1974 | Ahlberg et al. | 351/165 |
| 3,867,175 | 2/1975 | Dornte | 351/166 |
| 4,338,003 | 7/1982 | Adrian | 351/45 |
| 4,470,673 | 9/1984 | Gilson et al. | 351/44 |
| 4,758,079 | 7/1988 | Bledsoe | 351/44 |
| 4,919,529 | 4/1990 | Hyun | 351/50 |
| 4,989,967 | 2/1991 | Matsuda | 351/165 |

Primary Examiner—Huy Mai
Attorney, Agent, or Firm—Guido Modiano; Albert Josif; Daniel O'Byrne

[57] ABSTRACT

Multilayer lens particularly usable for sunglasses, having a main layer made of polycarbonate, cellulose acetate, or similar materials. A mirror reflecting layer is possibly coupled to the main layer or deposited thereon in vacuum by sublimation of appropriate substances, with the optional interposition of a layer of paint. The multilayer lens furthermore includes an outer layer that partially affects the outer surface of the lens. The lens may also include an inner antifogging layer that does not absorb moisture. This multilayer lens allows optimum vision to the user, eliminating or attenuating spurious incident rays at the lateral ends of the lens.

13 Claims, 2 Drawing Sheets

MULTILAYER LENS PARTICULARLY FOR SUNGLASSES

BACKGROUND OF THE INVENTION

The present invention relates to a multilayer lens particularly for sunglasses.

Various kinds of multilayer lenses are currently known and used for sunglasses which essentially comprise a central layer made of polycarbonate or cellulose acetate or similar materials.

An outer reflecting mirror layer is sometimes coupled to the central layer or is deposited thereon by sublimation of appropriate substances and with the possible interposition of a layer of paint.

A layer that absorbs any moisture, by retaining the moisture up to the saturation limit of the layer, is instead placed internally.

Some problems are observed if these conventional lenses must have a highly curved shape, and thus if the ends of the lens must affect the lateral regions of the user's temples: first of all, the dimensions of the lens are such that the user, while using the glasses, sees not only whatever is in his front viewing field but also the rays (hereinafter termed spurious) affecting the lens ends arranged laterally to his viewing field, thus creating unpleasant interference.

This interference is highly relevant as the user's concentration in sports practice increases, and this concentration must be maximum in use during competitions.

Furthermore, the use of an inner layer of antifogging material according to the described characteristics, and thus of a layer that gradually absorbs the moisture rising from the face, in any case causes a drawback: after some time, in fact, once the layer has saturated, the lens fogs again, forcing the user to remove his goggles to dry or defog them.

This condition certainly penalizes the user in all sports practices.

SUMMARY OF THE INVENTION

A principal aim of the present invention is therefore to eliminate the above described drawbacks in known types by providing a multilayer lens particularly for sunglasses which despite surrounding not only the central region but also, at least partially, the lateral regions of the viewing field, allows the user optimum vision not only of the front region but also partially of the lateral regions without being negatively affected by bothersome spurious rays.

An important object of the invention is to provide a multilayer lens which does not fog during sports practice.

Another object is to provide a multilayer lens which is reliable and safe in use and has modest manufacturing costs.

With this aim, these objects and others in view, there is provided, according to the invention, a multilayer lens which comprises a main layer made of polycarbonate, cellulose acetate, or similar materials, a reflecting layer possibly being coupled with said main layer, or deposited thereon in vacuum by sublimation of appropriate substances, with the interposition of at least one optional layer of paint, in which the lens is characterized in that it comprises an outer layer or a plurality of dead holes that partially affects the surface of said lens and at least partially darkens it. An inner antifogging layer that does not absorb moisture may also be provided.

BRIEF DESCRIPTION OF THE DRAWINGS

Further characteristics and advantages of the lens according to the invention will become apparent from the following detailed description of some preferred but not exclusive embodiments thereof, illustrated only by way of non-limitative example in the accompanying drawings, wherein.

DESCRIPTION OF THE PREFERRED EMBODIMENTS

Figure 1:
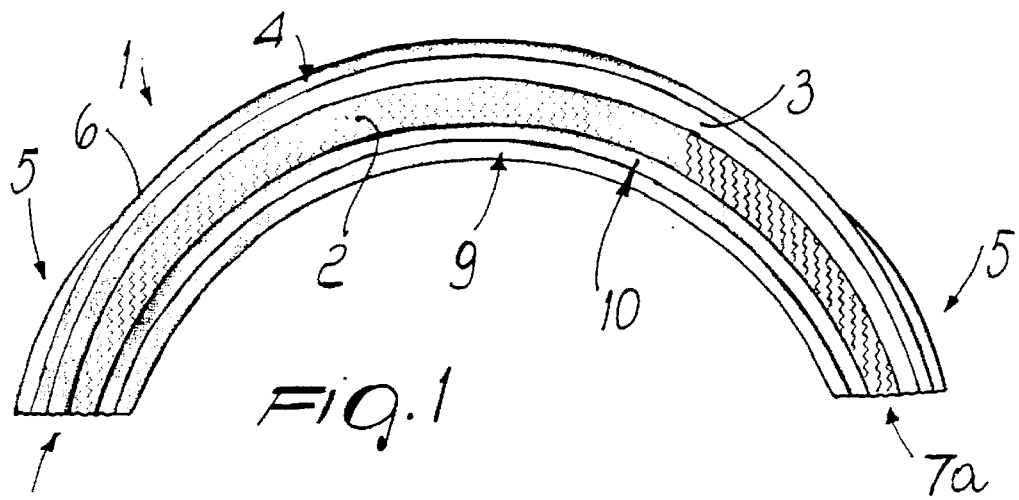
FIG. 1 is a sectional view of the various layers of the multilayer lens according to the invention.
Figure 2:
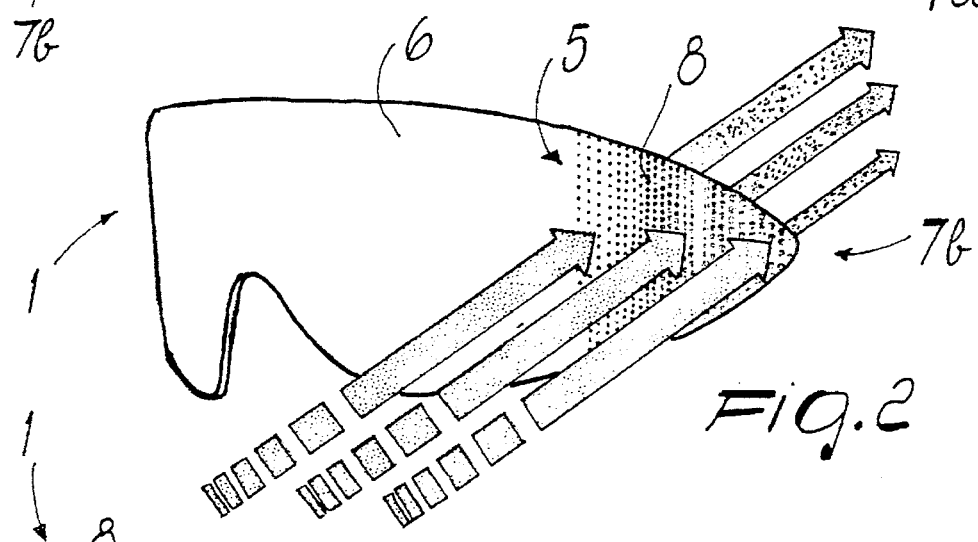
FIG. 2 is a lateral perspective view of the lens according to a first aspect of the invention; illustrating the use of the lens.
Figure 3:
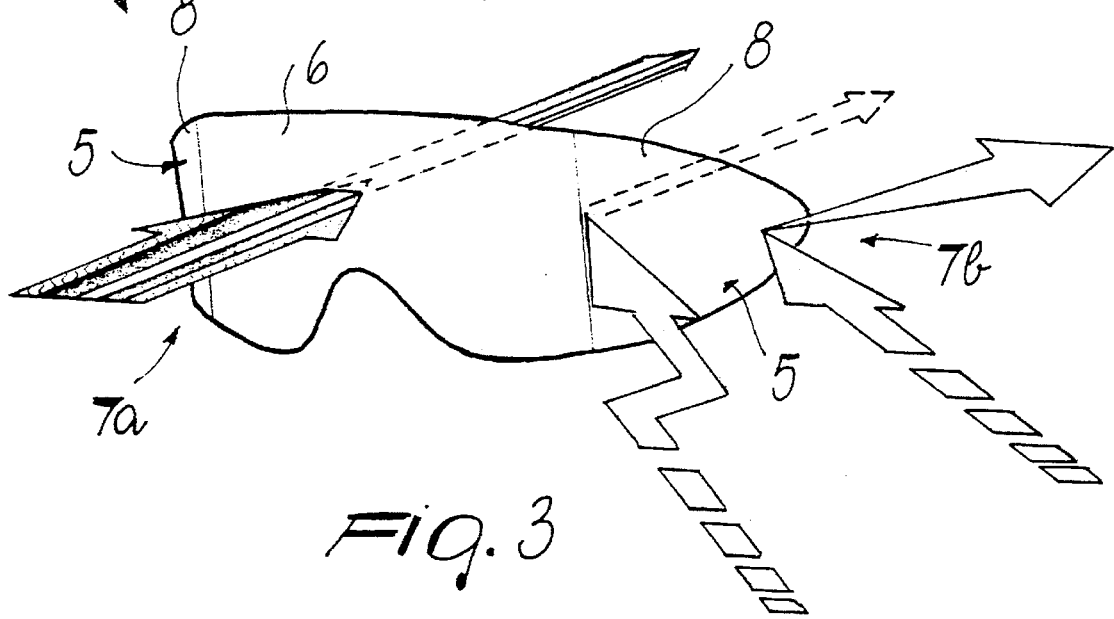

With reference to the above figures, the multilayer lens, generally designated by the reference numeral 1, essentially comprises a central layer 2 made of polycarbonate, cellulose acetate, or similar materials.

A reflecting mirror outer layer 4 may be coupled to the main layer 2, or deposited thereon in vacuum by sublimation of appropriate substances (preferably a mixture of chrome and silicon monoxide), with the possible interposition of at least one layer 3 of paint.

The multilayer lens 1 furthermore comprises at least one lateral or perimetric layer 5 which is arranged externally and partially affects the lateral region 6 of the lens, preferably at the ends 7a and 7b of the lens and at the regions adjacent to said ends towards the central region of the lens.

Said lateral layer 5 present at the lateral region 6 of the lens (and in the case illustrated present on the lateral surface of the outer layer 4) can be obtained by applying, by conventional color application methods such as silk-screen printing, transfer and preferably tamp-print, a plurality of covering elements, such as for example dots 8 of paint material whose size preferably decreases from the ends 7a and 7b of the lens towards the center thereof.

Figure 4:
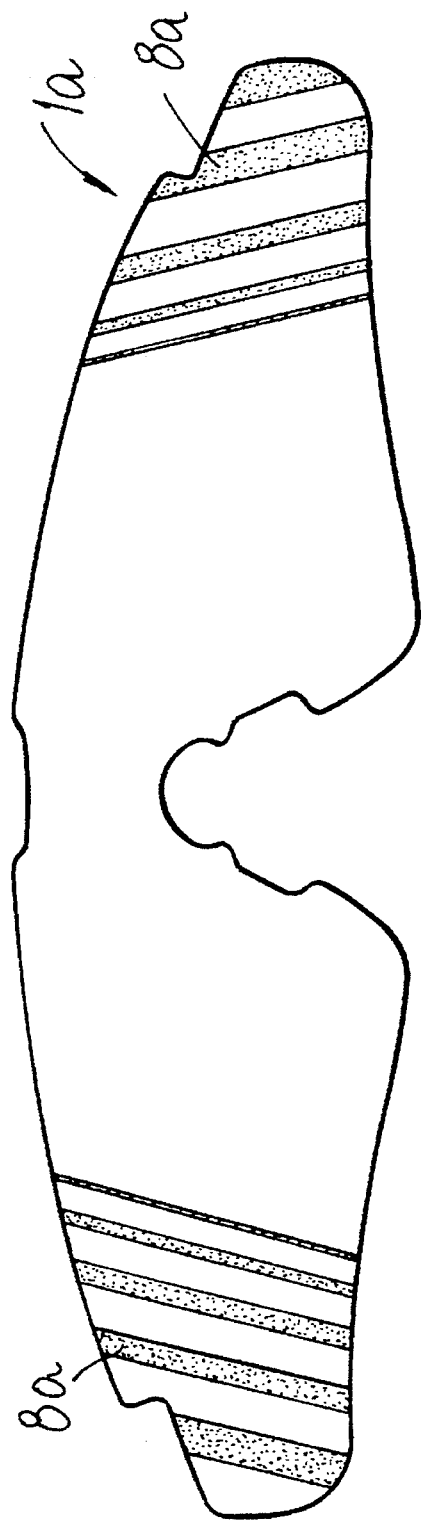
FIGS. 4 and 5 are schematic views of the lens according to further aspects of the present invention.

The dots 8 preferably have a circular shape but also dots of triangular shape have been envisaged. Alternatively, the layer 5 may be obtained by applying the paint material in the form of band elements 8a (FIG. 4) the width whereof preferably decreases from the lateral perimetric region of the lens 1a towards the central region thereof. The illustrated bands 8a are arranged mutually parallel. It has further been envisaged to employ mutually intersecting bands. Preferably, the paint material employed is an epoxy resin paint, applied with the tamp-print method.

Alternatively, a single band of paint material having a transparency which preferably decreases from the center of the lens towards the peripheral regions is provided at the layer 5. The lateral layer 5 can also be obtained by forming for example with laser techniques for removing material, at the lateral surface 6 of the outer layer 4, a plurality of dead holes or grooves which have the desired configuration in plan view and whose purpose, like the dots 8, is to filter the incident rays; this filtration effect increases as the diameter of said dots, band elements or grooves, increases so that said filtration effect is total at the ends and gradually decreases towards the center of the lens.

An additional function is to realign external spurious rays.

Figure 5:
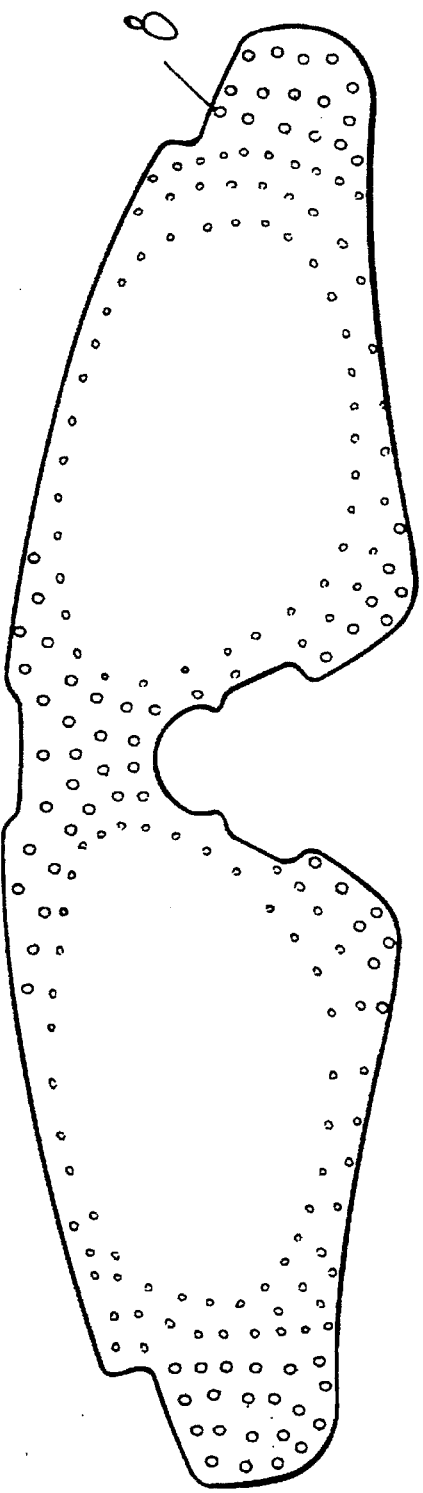

FIG. 5 shows a plurality of dots of paint material 8 provided in the peripheral zones, that is laterally, above and below, of the central zone of the lens which is the ocular zone of the user. The dots 8 decrease in size from the outermost regions towards the center. Thereby, the ratio of the area of paint with respect to the area void of paint decreases from the peripheral region towards the central region of the lens so that the degree of transparency decreases in the peripheral zone from points nearer to the center of the lens to points more distal to the center of the lens, similarly as obtained with the previously described embodiment including a single band of paint material having a transparency which decreases from the center of the lens towards the peripheral regions.

These solutions therefore allow to filter so-called spurious rays and thus eliminate the nuisance that they can cause to the user, allowing the user to achieve maximum concentration for example in use during competitions without limiting the viewing field of the user.

Of course, the area of the outer layer 5 that affects the lateral surface 6 of the outer layer 4 may be the most appropriate according to the specific requirements and thus according to the specific sports activity being performed.

The multilayer lens 1 is furthermore comprises an inner antifogging layer 9 which is applied at the inner surface of the layer 2 or at the inner surface of a layer 10, which is equivalent to the layer 4, applied at the inner surface of the layer 2.

Said inner antifogging layer 9 has antifogging properties, in the sense that it does not absorb the moisture present on it but repels it constantly, so as to achieve an antifogging effect that is constant in the course of time.

Preferably, the antifogging layer 9 comprises a polyester adhesive film, or alternatively a coating applied by immersion. In both cases the antifog effect is obtained by means of a variation in the surface tension which renders the inner surface treated in this manner repellent to moisture.

Use of the multilayer lens is thus as follows: once the goggles with which the lens is associated have been put on, the user is allowed optimum vision both in the central region of the lens and in the lateral regions thereof if they partially affect the user's temples.

The presence of the layer 5 in fact on one hand allows to prevent the passage of spurious external rays proximate to the end of said lens, and on the other hand filters part of these rays, realigning the plane of incidence.

The presence of the layer 9 instead allows, even during competitions, to avoid the fogging of the lens, allowing the user to optimally concentrate during sports practice.

It has thus been observed that the invention has achieved the above mentioned aim and objects, a multilayer lens having been obtained which despite surrounding not only the central region but also the lateral regions of the viewing field allows optimum vision to the user not only in the front region but also partially in the lateral regions, without being negatively affected by bothersome spurious rays, which are highly attenuated or reflected by the outer layer 5; the spurious rays affecting the layer 5 in a region thereof that does not coincide with the ends of the lens are furthermore realigned, in the sense that their angle of incidence is changed, returning it approximately parallel to the angle of incidence of the rays affecting the central region of the lens.

The layer 5 can have the most appropriate aesthetic configurations and a physical embodiment which is appropriate for the specific requirements of production.

The presence in the multilayer lens of the antifogging layer which does not absorb moisture, but constantly repels it, allows to practice sports in an optimum way with no fogging during said practice.

Another function performed by the layer 9 is to improve the mechanical characteristics of the lens so as to make it extremely safe for the user.

Another function of the layer 9 is, like plexiglass sheets, to prevent fragments of the lens from reaching the user's eyes in case of breakage of said lens.

The invention is naturally susceptible to numerous modifications and variations, all of which are within the scope of the same inventive concept.

The materials and the dimensions constituting the individual components of the lens according to the invention may naturally also be the most pertinent according to the specific requirements.

What is claimed is:

1. A lens for sunglasses, comprising:
   a main lens layer having at least one central view region and at least one lateral view region arranged adjacent said central view region, said central and lateral view regions being arranged such that a viewing field of a user includes said central and lateral view regions; and
   a transparency affecting element arranged at said lateral view region of said main lens layer such that a degree of transparency of the lens is greater at said central view region than at said lateral view region, and such that a degree of transparency of the lens in the lateral view region decreases from points nearer to the central view region to points arranged more distally to the central view region, wherein said transparency affecting element comprises a plurality of areas of said main lens layer at said lateral view region at which material has been removed from said main lens layer.

2. The lens of claim 1, wherein said main lens layer is made of a material chosen among polycarbonate material and cellulose acetate material.

3. The lens of claim 1, further comprising a mirror layer arranged externally to said main lens layer.

4. The lens of claim 3, further comprising a layer of paint interposed between said mirror layer and said main lens layer.

5. The lens of claim 1, further comprising a non-moisture absorbing and moisture repellent inner antifogging layer arranged internally to said main lens layer.

6. The lens of claim 5, further comprising a mirror layer interposed between said antifogging layer and said main lens layer.

7. The lens of claim 1, wherein said plurality of areas are in the shape of holes.

8. The lens of claim 1, wherein said plurality of areas are in the shape of grooves.

9. A lens for sunglasses, comprising:
   a main lens layer having at least one central view region and at least one lateral view region arranged adjacent said central view region said central and lateral view regions being arranged such that a viewing field of a user includes said central and lateral view regions; and
   a transparency affecting means arranged at said lateral view region of said main lens layer for creating a degree of transparency of the lens which is greater at said central view region than at said lateral view region and such that a degree of transparency of the lens in the lateral view region decreases from points nearer to the central view region to points arranged more distally to the central view region, wherein said transparency affecting means is formed by an area at said lateral view region where material has been removed from said main lens layer.

10. A lens for sunglasses, comprising:
    a main lens layer having at least one central view region and at least one lateral view region arranged adjacent said central view region said central and lateral view regions being arranged such that a viewing field of a user includes said central and lateral view regions;

a transparency affecting element arranged at said lateral view region of said main lens layer such that a degree of transparency of the lens is greater at said central view region than at said lateral view region; and a non-moisture absorbing and moisture repellent inner antifogging layer arranged internally to said main lens layer;

wherein said transparency affecting element is formed by an area at said lateral view region where material has been removed from said main lens layer.

11. The lens of claim 10, wherein said transparency affecting element arranged at said lateral view region of said main lens layer is such that a degree of transparency of the lens in the lateral view region decreases from points nearer to the central view region to points arranged more distally to the central view region.

12. A lens for sunglasses, comprising:

a main lens layer having at least one central view region and at least one lateral view region arranged adjacent said central view region said central and lateral view regions being arranged such that a viewing field of a user includes said central and lateral view regions;

a transparency affecting element arranged at said lateral view region of said main lens layer such that a degree of transparency of the lens is greater at said central view region than at said lateral view region;

a mirror layer arranged externally to said main lens layer;

an inner antifogging layer arranged internally to said main lens layer;

a layer of paint interposed between said mirror layer and said main lens layer; and a mirror layer interposed between said antifogging layer and said main lens layer;

wherein said transparency affecting element is formed by an area at said lateral view region where material has been removed from said main lens layer.

13. The lens of claim 12, wherein said transparency affecting element arranged at said lateral view region of said main lens layer is such that a degree of transparency of the lens in the lateral view region decreases from points nearer to the central view region to points arranged more distally to the central view region.

* * * * *